(12) United States Patent
Audousset

(10) Patent No.: US 7,306,630 B2
(45) Date of Patent: *Dec. 11, 2007

(54) COMPOSITION COMPRISING AT LEAST ONE COUPLER CHOSEN FROM 2-CHLORO-6-METHYL-3-AMINOPHENOL AND ADDITION SALTS THEREOF, AT LEAST ONE OXIDATION BASE, AND AT LEAST ONE ASSOCIATIVE POLYMER COMPRISING AT LEAST ONE $C_8$-$C_{30}$ FATTY CHAIN

(75) Inventor: Marie-Pascale Audousset, Asnieres (FR)

(73) Assignee: L'Oreal S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/834,349

(22) Filed: Apr. 29, 2004

(65) Prior Publication Data

US 2005/0000039 A1 Jan. 6, 2005

Related U.S. Application Data

(60) Provisional application No. 60/507,115, filed on Oct. 1, 2003.

(30) Foreign Application Priority Data

Apr. 29, 2003 (FR) .................................. 03 05242

(51) Int. Cl.
*A61K 7/13* (2006.01)

(52) U.S. Cl. .................. 8/405; 8/406; 8/410; 8/411; 8/421; 8/424; 8/515; 8/552; 8/554

(58) Field of Classification Search .................. 8/405, 8/406, 410, 411, 421, 424, 515, 552, 554
See application file for complete search history.

(56) References Cited

U.S. PATENT DOCUMENTS

| | | | |
|---|---|---|---|
| 3,915,921 A | 10/1975 | Schlatzer, Jr. .............. | 266/17.4 |
| RE30,199 E | 1/1980 | Rose et al. .................... | 8/10.2 |
| 4,509,949 A | 4/1985 | Huang et al. ............... | 286/558 |
| 4,823,985 A | 4/1989 | Grollier et al. ................ | 222/1 |
| 5,061,289 A | 10/1991 | Clausen et al. ............... | 8/405 |
| 5,380,340 A | 1/1995 | Neunhoeffer et al. .......... | 8/405 |
| 5,534,267 A | 7/1996 | Neunhoeffer et al. ....... | 424/201 |
| 5,663,366 A | 9/1997 | Neunhoeffer et al. .... | 548/371.4 |
| 5,766,576 A | 6/1998 | Löwe .......................... | 424/67 |
| 6,099,592 A | 8/2000 | Vidal et al. .................... | 8/409 |
| 6,156,076 A | 12/2000 | Casperson ..................... | 8/406 |
| 6,277,156 B1* | 8/2001 | Audousset ..................... | 8/407 |
| 6,284,003 B1 | 9/2001 | Rose et al. .................... | 8/412 |
| 6,338,741 B1 | 1/2002 | Vidal et al. .................... | 8/409 |
| 6,379,396 B1 | 4/2002 | Audousset ..................... | 8/407 |
| 6,436,151 B2 | 8/2002 | Cottard et al. ................. | 8/406 |
| 6,503,282 B1 | 1/2003 | Braun ............................ | 8/405 |
| 6,645,258 B2 | 11/2003 | Vidal et al. .................... | 8/405 |
| 6,730,789 B1 | 5/2004 | Birault et al. ............... | 546/121 |
| 2001/0023514 A1* | 9/2001 | Cottard et al. ................. | 8/406 |
| 2001/0023515 A1 | 9/2001 | Cottard et al. ................. | 8/406 |
| 2001/0047554 A1 | 12/2001 | Mettrie et al. ................. | 8/405 |
| 2002/0050013 A1 | 5/2002 | Vidal et al. .................... | 8/405 |
| 2003/0019051 A9 | 1/2003 | Vidal et al. .................... | 8/405 |
| 2003/0106167 A1 | 6/2003 | Rose et al. .................... | 8/405 |
| 2003/0124079 A1 | 7/2003 | Mougin et al. .......... | 424/20.11 |
| 2003/0172471 A1 | 9/2003 | Chassot et al. ................ | 8/405 |
| 2004/0025266 A1 | 2/2004 | Cottard et al. ................. | 8/405 |
| 2004/0049860 A1 | 3/2004 | Cottard et al. ................. | 8/405 |
| 2004/0141943 A1 | 7/2004 | Mougin et al. .......... | 424/70.17 |
| 2004/0205901 A1 | 10/2004 | Cottard et al. ................. | 8/405 |
| 2005/0076458 A1 | 4/2005 | Cottard et al. ................. | 8/405 |

FOREIGN PATENT DOCUMENTS

| | | |
|---|---|---|
| DE | 23 59 399 | 6/1975 |
| DE | 30 16 008 | 10/1981 |
| DE | 38 43 892 A1 | 6/1990 |
| DE | 41 33 957 A1 | 4/1993 |
| DE | 195 43 988 A1 | 5/1997 |
| DE | 201 07 481 | 7/2001 |
| DE | 201 18 982 | 2/2002 |
| EP | 0 216 479 B2 | 4/1987 |
| EP | 0 173 109 | 10/1989 |
| EP | 0 770 375 | 5/1997 |
| EP | 0 875 237 A2 | 11/1998 |

(Continued)

OTHER PUBLICATIONS

English language Derwent Abstract of DE 30 16 008, Oct. 29, 1981.
English language Derwent Abstract of DE 201 18 982, Feb. 28, 2002.
English language Derwent Abstract of FR 2 802 089, Jun. 15, 2001.
Co-pending U.S. Appl. No. 10/834,113, filed Apr. 29, 2004, Title: Dye Composition Comprising 2-Chloro-6-Methyl-3-Aminophenol as Coupler, Para-Aminophenol and 3-Methyl-4-Aminophenol as Oxidation Bases and at Least One Associative Thickening Polymer.
Co-pending U.S. Appl. No. 10/834,270, filed Apr. 29, 2004, Title: Omposition Comprising at Least One Coupler Chosen From 2-Chloro-6-Methyl-3-Aminophenol and Addition Salts Thereof, At Least One Oxidation Base, and At Least One Associative Polymer Comprising at Least One C8-C30 Fatty Chain.
Office Action in co-pending U.S. Appl. No. 10/834,113, dated Mar. 29, 2005.
Office Action in co-pending U.S. Appl. No. 10/834,270, dated Mar. 29, 2005.

(Continued)

*Primary Examiner*—Eisa Elhilo
(74) *Attorney, Agent, or Firm*—Finnegan, Henderson, Farabow, Garrett & Dunner, LLP

(57) ABSTRACT

A composition comprising at least one coupler chosen from 2-chloro-6-methyl-3-aminophenol and addition salts thereof, at least one oxidation base and at least one associative polymer comprising at least one $C_8$-$C_{30}$ fatty chain; the use of the composition for the oxidation dyeing of keratin fibres; the dyeing process using this composition; and multi-compartment devices comprising the composition.

49 Claims, No Drawings

FOREIGN PATENT DOCUMENTS

| | | |
|---|---|---|
| FR | 2586913 | 3/1987 |
| FR | 2733749 | 11/1996 |
| FR | 2801308 | 5/2001 |
| FR | 2 802 089 | 6/2001 |
| FR | 2 811 993 | 1/2002 |
| FR | 2 820 032 | 8/2002 |
| GB | 1026978 | 4/1966 |
| GB | 1153196 | 5/1969 |
| JP | 2-019576 | 1/1990 |
| JP | 10-508861 | 9/1998 |
| JP | 10-508862 | 9/1998 |
| JP | 10-316546 | 12/1998 |
| JP | 2001/206828 | 7/2001 |
| JP | 2001/220330 | 8/2001 |
| JP | 2002-509099 | 10/2001 |
| WO | WO 94/08969 | 4/1994 |
| WO | WO 94/08970 | 4/1994 |
| WO | WO 96/15765 | 5/1996 |
| WO | WO 96/15766 | 5/1996 |
| WO | WO 98/03150 | 1/1998 |
| WO | WO 98/44012 | 10/1998 |
| WO | WO 99/11229 A | 3/1999 |
| WO | WO 00/68282 | 11/2000 |
| WO | WO 01/41717 | 6/2001 |
| WO | WO 01/78668 A | 10/2001 |
| WO | WO 2002/00181 A1 | 1/2002 |
| WO | WO 02/22095 | 3/2002 |
| WO | WO 2002/38116 A1 | 5/2002 |
| WO | WO 2002/45673 A2 | 6/2002 |
| WO | WO 02/076923 | 10/2002 |
| WO | WO 02/096382 | 12/2002 |
| WO | WO 03/017956 | 3/2003 |

OTHER PUBLICATIONS

English language Derwent Abstract of DE 201 07 481, Jul. 12, 2001.
English language Derwent Abstract of EP 0 770 375, May 2, 1997.
English language Derwent Abstract of JP 2-019576 (88-169571), Jan. 23, 1990.
English language Derwent Abstract of WO 02/096382, Dec. 5, 2002.
French Search Report for FR 03 05243, Jan. 20, 2004.
French Search Report for FR 03 05241, Feb. 11, 2004.
French Search Report for FR 03 05242, Feb. 12, 2004.
G. Fonnum, J. Bakke and Fk. Hansen—Colloid Polym. Sci 271, 380-389 (1993).
European Search Report for EP 04 291 086 (European counterpart to U.S. Appl. No. 10/834,270) dated Jul. 9, 2004.
European Search Report for EP 04 291 095 (European counterpart to U.S. Appl. No. 10/834,349) dated Jul. 9, 2004.
English language Derwent Abstract of JP 10-508862, Sep. 2, 1998.

\* cited by examiner

COMPOSITION COMPRISING AT LEAST ONE COUPLER CHOSEN FROM 2-CHLORO-6-METHYL-3-AMINOPHENOL AND ADDITION SALTS THEREOF, AT LEAST ONE OXIDATION BASE, AND AT LEAST ONE ASSOCIATIVE POLYMER COMPRISING AT LEAST ONE $C_8$-$C_{30}$ FATTY CHAIN

This application claims benefit of U.S. Provisional Application No. 60/507,115, filed Oct. 1, 2003.

Disclosed herein are compositions for the oxidation dyeing of keratin fibres, for example, human keratin fibres such as hair, comprising at least one coupler chosen from 2-chloro-6-methyl-3-aminophenol and addition salts thereof, at least one oxidation base, and at least one associative polymer comprising at least one $C_8$-$C_{30}$ fatty chain.

It is known practice to dye keratin fibres, for example, human keratin fibres such as hair, with dye compositions comprising oxidation dye precursors, which are generally known as oxidation bases, such as ortho- and para-phenylenediamines, ortho- and para-aminophenols and heterocyclic compounds. These oxidation bases are colorless or weakly colored compounds that, when combined with oxidizing products, may give rise to colored compounds by a process of oxidative condensation.

It is also known that the shades obtained with these oxidation bases may be varied by combining them with couplers or coloration modifiers. The couplers or coloration modifiers may be chosen, for example, from aromatic meta-diamines, meta-aminophenols, meta-diphenols and certain heterocyclic compounds such as indole compounds.

The variety of molecules used as oxidation bases and couplers may allow a wide range of colors to be obtained.

These oxidation bases and couplers may be formulated in supports that allow them to be applied to keratin fibres after mixing with an oxidizing agent.

To localize the oxidation dye product for application to the hair so that it does not run down the face or beyond the areas that it is intended to dye, conventional thickeners may be introduced into these supports, such as crosslinked polyacrylic acid, hydroxyethylcelluloses, waxes and mixtures of suitably selected nonionic surfactants with an HLB (hydrophilic-lipophilic balance), and also nonionic, anionic, cationic and amphoteric associative polymers.

In some embodiments, the "permanent" coloration obtained with these oxidation dyes should also satisfy a certain number of requirements. For example, it may satisfy at least one of the following requirements: have no toxicological drawbacks; allow shades to be obtained in the desired intensity; show good resistance to external agents such as light, bad weather, washing, permanent-waving, perspiration and rubbing; allow white hairs to be covered; and be as unselective as possible, i.e. they must produce the smallest possible color differences along the same length of keratin fiber, that may in fact be differently sensitized (i.e. damaged) between its end and its root.

Compositions for the oxidation dyeing of keratin fibres, comprising 2-chloro-6-methyl-3-aminophenol or 2-methyl-6-chloro-3-aminophenol as a coupler, in combination with oxidation bases conventionally used for oxidation dyeing, for example, certain para-phenylenediamines, para-aminophenol or heterocyclic bases, have already been proposed, for example, in German Patent Application No. DE 30 16 008.

Patent Application No. WO 96/15765 describes compositions for the oxidation dyeing of keratin fibres, comprising 2-chloro-6-methyl-3-aminophenol as a coupler and 2-(2,5-diaminophenyl)ethanol as a oxidation base.

Patent Application No. WO 96/15766 describes compositions for the oxidation dyeing of keratin fibres comprising 2-chloro-6-methyl-3-aminophenol as a coupler and, for example, oxidation bases chosen from para-aminophenol derivatives substituted in position 2 or 3, for example, 3-methyl-4-aminophenol, 2-allyl-4-aminophenol or 2-aminomethyl-4-aminophenol.

However, these compositions may not be entirely satisfactory, for example, with regard to the staying power of the colorations obtained. For example, these compositions may not be resistant to the various attacking factors to which the hair may be subjected, such as shampoo, light, sweat and permanent-reshaping operations. Further, for example, the strength and chromaticity of the colorations obtained with these compositions may also not be satisfactory.

The aim of the present inventor was to provide novel compositions for the oxidation dyeing of keratin fibres that, in some embodiments, overcome at least one drawback of the prior part. For example, in one embodiment, the compositions may produce strong, chromatic, aesthetic colorations in varied shades, which may also show little selectivity and good resistance to the various attacking factors to which the hair may be subjected, such as shampoo, light, sweat and permanent-reshaping operations. In one embodiment, at least one of these aims may be achieved with the compositions disclosed herein.

Disclosed herein is composition comprising, in a suitable dyeing medium:
- at least one coupler chosen from 2-chloro-6-methyl-3-aminophenol and addition salts thereof;
- at least one oxidation base; and
- at least one associative polymer comprising at least one $C_8$-$C_{30}$ fatty chain. In one embodiment, the compositions are for the oxidation dyeing of keratin fibres.

The compositions disclosed herein may, for example, allow a more intense and more chromatic, less selective and fast coloration of keratin fibres to be obtained.

Further disclosed herein is a process for the oxidation dyeing of keratin fibres, for example, human keratin fibres, such as hair, using the compositions.

Even further disclosed herein is the use of the compositions disclosed herein for the oxidation dyeing of keratin fibres, for example, human keratin fibres, such as hair.

The at least one oxidation base that may be used in the compositions disclosed herein may, for example, be chosen from para-phenylenediamines, double bases, para-aminophenols, ortho-aminophenols and heterocyclic oxidation bases, and addition salts thereof.

The para-phenylenediamines that may be used in the compositions disclosed herein may, for example, be chosen from compounds of formula (I), and addition salts thereof:

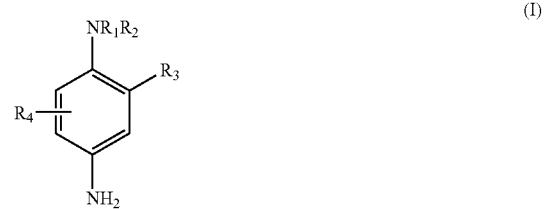

wherein:
- R₁ is chosen from a hydrogen atom, $C_1$-$C_4$ alkyl radicals, $C_1$-$C_4$ monohydroxyalkyl radicals, $C_2$-$C_4$ polyhydroxyalkyl radicals, ($C_1$-$C_4$)alkoxy($C_1$-$C_4$)alkyl radicals, $C_1$-$C_4$ alkyl radicals substituted with at least one nitrogenous group, a phenyl radical, and a 4'-aminophenyl radical;
- R₂ is chosen from a hydrogen atom, $C_1$-$C_4$ alkyl radicals, $C_1$-$C_4$ monohydroxyalkyl radicals, $C_2$-$C_4$ polyhydroxyalkyl radicals, ($C_1$-$C_4$)alkoxy($C_1$-$C_4$)alkyl radicals, and $C_1$-$C_4$ alkyl radicals substituted with at least one nitrogenous group;
- R₁ and R₂ may form, together with the nitrogen atom to which they are attached, a heterocycle chosen from 5- to 8-membered heterocycles optionally substituted with at least one group chosen from $C_1$-$C_4$ alkyl radicals, hydroxyalkyl radicals and $C_1$-$C_4$ trialkylammonium radicals;
- R₃ is chosen from a hydrogen atom, halogen atoms, such as a chlorine, bromine, iodine and fluorine atoms, $C_1$-$C_4$ alkyl radicals, $C_1$-$C_4$ monohydroxyalkyl radicals, $C_1$-$C_4$ hydroxyalkoxy radicals, acetylamino($C_1$-$C_4$)alkoxy radicals, mesylamino($C_1$-$C_4$)alkoxy radicals, and carbamoylamino($C_1$-$C_4$)alkoxy radicals; and
- R₄ is chosen from a hydrogen atom, halogen atoms, and $C_1$-$C_4$ alkyl radicals.

Examples of the para-phenylenediamines of formula (I) include para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-N,N-bis(β-hydroxyethyl)-2-chloroaniline, 2-(β-hydroxyethyl)-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-(β-hydroxyethyloxy)-para-phenylenediamine, 2-(β-acetylaminoethyloxy)-para-phenylenediamine, N-(β-methoxyethyl)-para-phenylenediamine, 2-(β-hydroxyethyl)amino-5-aminotoluene, and addition salts thereof.

In one embodiment, para-phenylenediamines of formula (I) chosen from para-phenylenediamine, para-tolylenediamine, 2-isopropyl-para-phenylenediamine, 2-(β-hydroxyethyl)-para-phenylenediamine, 2-(β-hydroxyethyloxy)-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-(β-acetylaminoethyloxy)-para-phenylenediamine, and addition salts thereof, may be used in the compositions disclosed herein.

As used herein, the term "double bases" means compounds comprising at least two aromatic nuclei bearing at least one group chosen from amino and hydroxyl groups.

The double bases that may be used in the compositions disclosed herein may, for example, be chosen from compounds corresponding to formula (II) below and addition salts thereof:

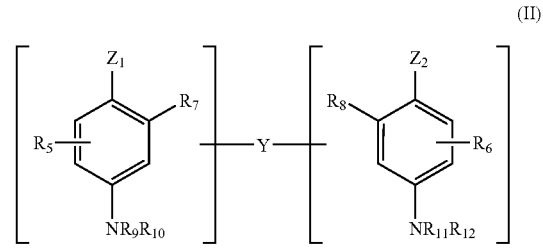

(II)

wherein:
- Z₁ and Z₂, which may be identical or different, are each chosen from hydroxyl radicals and amino radicals optionally substituted with at least one entity chosen from $C_1$-$C_4$ alkyl radicals and linker arm Y;
- linker arm Y is chosen from linear and branched alkylene chains comprising from 1 to 14 carbon atoms, wherein the alkylene chains may be interrupted by or terminated with at least one entity chosen from nitrogenous groups and hetero atoms, such as oxygen, sulphur and nitrogen atoms, and optionally substituted with at least one radical chosen from hydroxyl radicals and $C_1$-$C_6$ alkoxy radicals;
- R₅ and R₆, which may be identical or different, are each chosen from a hydrogen atom, halogen atoms, $C_1$-$C_4$ alkyl radicals, $C_1$-$C_4$ monohydroxyalkyl radicals, $C_2$-$C_4$ polyhydroxyalkyl radicals, $C_1$-$C_4$ aminoalkyl radicals, and linker arm Y; and
- R₇, R₈, R₉, R₁₀, R₁₁ and R₁₂, which may be identical or different, are each chosen from a hydrogen atom, linker arm Y, $C_1$-$C_4$ alkyl radicals, and $C_1$-$C_4$ monohydroxyalkyl radicals;

it being understood that the compounds of formula (II) comprise only one linker arm Y per molecule.

Examples of the double bases of formula (II) derived from para-phenylenediamine include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4'-aminophenyl)tetramethylenediamine, N,N'-bis(β-hydroxyethyl)-N,N'-bis(4'-aminophenyl)tetramethylenediamine, N,N'-bis(4'-methylaminophenyl)-tetramethylenediamine, N,N'-bis(ethyl)-N,N'-bis(4'-amino-3'-methylphenyl)ethylenediamine, 1,8-bis(2',5'-diaminophenoxy)-3,6-dioxaoctane, and addition salts thereof.

For example, the double bases of formula (II) above chosen from para-aminophenol, 4-amino-6-[(5'-amino-2'-hydroxy-3'-methylphenyl)methyl]-2-methylphenol, bis(5'-amino-2'-hydroxyphenyl)methane, and addition salts thereof may be used in the compositions disclosed herein.

In one embodiment, the double bases of formula (II) chosen from N,N'-bis(β-hydroxyethyl)-N,N'-bis(4'-aminophenyl)-1,3-diaminopropanol, 1,8-bis(2,5-diaminophenoxy)-3,5-dioxaoctane, and addition salts thereof may be used in the compositions disclosed herein.

The para-aminophenols that may be used in the compositions disclosed herein may be chosen from compounds corresponding to formula (III) below, and addition salts thereof:

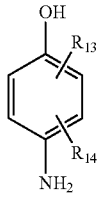
(III)

wherein:
R$_{13}$ is chosen from a hydrogen atom, halogen atoms, and C$_1$-C$_4$ alkyl radicals, C$_1$-C$_4$ monohydroxyalkyl radicals, (C$_1$-C$_4$)alkoxy(C$_1$-C$_4$)alkyl radicals, C$_1$-C$_4$ aminoalkyl radicals and hydroxy(C$_1$-C$_4$)alkylamino(C$_1$-C$_4$)alkyl radicals and R$_{14}$ is chosen from a hydrogen atom, halogen atoms, and C$_1$-C$_4$-alkyl radicals, C$_1$-C$_4$ monohydroxyalkyl radicals, C$_2$-C$_4$ polyhydroxyalkyl radicals, C$_1$-C$_4$ aminoalkyl radicals, C$_1$-C$_4$ cyanoalkyl radicals and (C$_1$-C$_4$)alkoxy-(C$_1$-C$_4$)alkyl radicals;

it being understood that at least one of the radicals R$_{13}$ and R$_{14}$ is a hydrogen atom.

Examples of the para-aminophenols of formula (III) above include para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, 4-amino-2-chlorophenol, 4-amino-2,6-dichlorophenol, and addition salts thereof.

Examples of ortho-aminophenols that may be used as the at least one oxidation base in the compositions disclosed herein include 2-aminophenol, 2-amino-5-methylphenol, 2-amino-6-methylphenol, 5-acetamido-2-aminophenol, and addition salts thereof.

Examples of heterocyclic bases that may be used as the at least one oxidation base in the compositions disclosed herein include pyridine derivatives, pyrimidine derivatives, pyrazole derivatives, pyrazolopyrimidine derivatives, and addition salts thereof.

Examples of pyridine derivatives that may be used as the at least one oxidation base include the compounds described, for example, in Patent Nos. GB 1 026 978 and GB 1 153 196, such as 2,5-diaminopyridine, 2-(4-methoxyphenyl)amino-3-aminopyridine, 2,3-diamino-6-methoxypyridine, 2-(β-methoxy-ethyl)amino-3-amino-6-methoxypyridine, 3,4-diaminopyridine, and addition salts thereof.

Further examples of pyridine derivatives that may be used include the 3-aminopyrazolo[1,5-a]pyridine oxidation bases and addition salts thereof described, for example, in Patent Application No. FR 2 801 308. For example, mention may be made of pyrazolo[1,5-a]pyrid-3-ylamine; 2-acetylaminopyrazolo[1,5-a]pyrid-3-ylamine; 2-morpholin-4-ylpyrazolo[1,5-a]pyrid-3-ylamine; 3-aminopyrazolo[1,5-a]pyridine-2-carboxylic acid, 2-methoxypyrazolo[1,5-a]pyrid-3-ylamine; (3-aminopyrazolo[1,5-a]pyrid-7-yl)methanol; 2-(3-aminopyrazolo[1,5-a]pyrid-5-yl)ethanol; 2,3-diaminopyrazolo[1,5-a]pyrid-7-yl)ethanol; (3-aminopyrazolo[1,5-a]pyrid-2-yl)methanol; 3,6-diaminopyrazolo[1,5-a]pyridine; 3,4-diaminopyrazolo[1,5-a]pyridine; pyrazolo[1,5-a]pyridine-3,7-diamine; 7-morpholin-4-ylpyrazolo[1,5-a]pyrid-3-ylamine; pyrazolo[1,5-a]pyridine-3,5-diamine; 5-morpholin-4-ylpyrazolo[1,5-a]pyrid-3-ylamine; 2-[(3-aminopyrazolo[1,5-a]pyrid-5-yl)(2-hydroxyethyl)amino]ethanol; 2-[(3-aminopyrazolo[1,5-a]pyrid-7-yl)-(2-hydroxyethyl)amino]ethanol; 3-aminopyrazolo[1,5-a]pyrid-5-ol; 3-aminopyrazolo[1,5-a]pyrid-4-ol; 3-aminopyrazolo[1,5-a]pyrid-6-ol; 3-aminopyrazolo-[1,5-a]pyrid-7-ol; and addition salts thereof.

Examples of pyrimidine derivatives that may be used as the at least one oxidation base include the compounds described, for example, in German Patent No. DE 23 59 399 and Japanese Patent Nos. JP 88-169571; JP 05-63124; EP 0 770 375 and Patent Application No. WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and addition salts thereof and the tautomeric forms thereof, when a tautomeric equilibrium exists.

Examples of pyrazole derivatives that may be used as the at least one oxidation base include the compounds described in Patent Nos. DE 38 43 892 and DE 41 33 957 and Patent Application Nos. WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-(β-hydroxyethyl)-3-methylpyrazole, 4,5-diamino-1-tert-butyl-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and addition salts thereof.

Examples of pyrazolopyrimidine derivatives that may be used in the compositions disclosed herein include pyrazolo[1,5-a]pyrimidines of formula (IV), and addition salts thereof with an acid or with a base and the tautomeric forms thereof, when a tautomeric equilibrium exists:

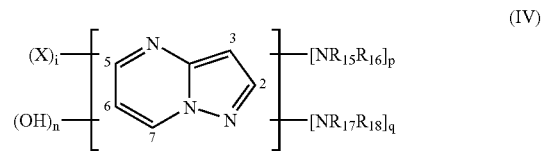
(IV)

wherein:
R$_{15}$, R$_{16}$, R$_{17}$ and R$_{18}$, which may be identical or different, are each chosen from a hydrogen atom, C$_1$-C$_4$ alkyl radicals, an aryl radial, C$_1$-C$_4$ hydroxyalkyl radicals, C$_2$-C$_4$ polyhydroxyalkyl radicals, (C$_1$-C$_4$)alkoxy(C$_1$-C$_4$)alkyl radicals, C$_1$-C$_4$ aminoalkyl radicals (it being possible for the amine to be substituted with at least one radical chosen from acetyl, ureido and sulphonyl radicals), (C$_1$-C$_4$)alkylamino(C$_1$-C$_4$)alkyl radicals, di[(C$_1$-C$_4$)alkyl]amino(C$_1$-C$_4$)alkyl radicals (it being possible for the dialkyl radicals to form a ring chosen from 5- and 6-membered carbon-based rings and heterocyclic rings), hydroxy($C_1$-$C_4$)alkyl- and di[hydroxy-($C_1$-$C_4$)alkyl]amino($C_1$-$C_4$)alkyl radicals;

radicals X, which may be identical or different, are each chosen from a hydrogen atom, $C_1$-$C_4$ alkyl radicals, an aryl radical, $C_1$-$C_4$ hydroxyalkyl radicals, $C_2$-$C_4$ polyhydroxyalkyl radicals, $C_1$-$C_4$ aminoalkyl radicals, ($C_1$-$C_4$)alkylamino($C_1$-$C_4$)alkyl radicals, di[($C_1$-$C_4$)alkyl]amino($C_1$-$C_4$)alkyl radicals (it being possible for the dialkyls to form a ring chosen from 5- and 6-membered carbon-based rings and heterocyclic rings), hydroxy ($C_1$-$C_4$)alkyl- and di[hydroxy($C_1$-$C_4$)alkyl]amino($C_1$-$C_4$)alkyl radicals, an amino radical, ($C_1$-$C_4$)alkyl- and di[($C_1$-$C_4$)alkyl]amino radicals; halogen atoms, a carboxylic acid group and a sulphonic acid group;

i is a number equal to 0, 1, 2 or 3;
p is a number equal to 0 or 1;
q is a number equal to 0 or 1; and
n is a number equal to 0 or 1;

with the proviso that:
the sum p+q is not 0;
when p+q is equal to 2, then n is equal to 0 and the groups $NR_{15}R_{16}$ and $NR_{17}R_{18}$ occupy the (2,3); (5,6); (6,7); (3,5) or (3,7) positions; and
when p+q is equal to 1, then n is equal to 1 and the group $NR_{15}R_{16}$ (or $NR_{17}R_{18}$) and the OH group occupy the (2,3); (5,6); (6,7); (3,5) or (3,7) positions.

When the pyrazolo[1,5-a]pyrimidines of formula (IV) above are such that they comprise a hydroxyl group on one of the positions 2, 5 or 7 α to a nitrogen atom, a tautomeric equilibrium exists represented, for example, by the following scheme:

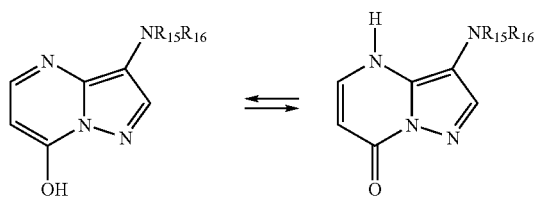

Examples of the pyrazolo[1,5-a]pyrimidines of formula (IV) above include pyrazolo[1,5-a]pyrimidine-3,7-diamine, 2,5-dimethylpyrazolo[1,5-a]pyrimidine-3,7-diamine, pyrazolo[1,5-a]pyrimidine-3,5-diamine, 2,7-dimethylpyrazolo[1,5-a]pyrimidine-3,5-diamine, 3-aminopyrazolo[1,5-a]pyrimidin-7-ol, 3-aminopyrazolo[1,5-a]pyrimidin-5-ol, 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimid in-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine, and addition salts thereof and the tautomeric forms thereof, when a tautomeric equilibrium exists.

The pyrazolo[1,5-a]pyrimidines of formula (IV) above can be prepared by cyclization starting with an aminopyrazole, according to the syntheses described in the following references:
EP 628559 Beiersdorf-Lilly;
R. Vishdu, H. Navedul, Indian J. Chem., 34b (6), 514, 1995;

N. S. Ibrahim, K. U. Sadek, F. A. Abdel-AI, Arch. Pharm., 320, 240, 1987;
R. H. Springer, M. B. Scholten, D. E. O'Brien, T. Novinson, J. P. Miller, R. K. Robins, J. Med. Chem., 25, 235, 1982;
T. Novinson, R. K. Robins, T. R. Matthews, J. Med. Chem., 20, 296, 1977; and
U.S. Pat. No. 3,907,799 ICN Pharmaceuticals.

The pyrazolo[1,5-a]pyrimidines of formula (IV) above can also be prepared by cyclization starting from hydrazine, according to the syntheses described in the following references:
A. McKillop and R. J. Kobilecki, Heterocycles, 6(9), 1355, 1977;
E. Alcade, J. De Mendoza, J. M. Marcia-Marquina, C. Almera, J. Elguero, J. Heterocyclic Chem., 11(3), 423, 1974; and
K. Saito, I. Hori, M. Higarashi, H. Midorikawa, Bull. Chem. Soc. Japan, 47(2), 476, 1974.

The at least one associative polymer comprising at least one $C_8$-$C_{30}$ fatty chain that may be used in the compositions disclosed herein may be chosen from water-soluble and water-dispersible polymers capable, in an aqueous medium, of reversibly associating together or with other molecules.

The at least one associative polymer comprising at least one $C_8$-$C_{30}$ fatty chain comprises at least one hydrophilic region and at least one hydrophobic region, i.e., the at least one $C_8$-$C_{30}$ fatty chain, or, for example, at least one $C_{10}$-$C_{30}$ fatty chain.

The at least one associative polymer comprising at least one $C_8$-$C_{30}$ fatty chain may be derived from free-radical polymerization; polycondensation starting with at least one monomer, wherein at least one of the monomers comprises at least one $C_8$-$C_{30}$ fatty chain, for example, at least one $C_{10}$-$C_{30}$ fatty chain; or grafting onto a polymer, for example, a polyhydroxylated polymer, a compound comprising at least one $C_8$-$C_{30}$ fatty chain, for example, at least one $C_{10}$-$C_{30}$ fatty chain.

In one embodiment, the at least one associative polymer comprising at least one $C_8$-$C_{30}$ fatty chain that may be used in the compositions disclosed herein is chosen from thickening polymers.

As used herein, the term "thickening polymer" means a polymer that has, as a solution or a dispersion at 5% by weight of active material in water, a viscosity measured using a Rheomat RM 180 rheometer, at 25° C., equal to at least one 500 cP, at a shear rate of 100 s$^{-1}$.

The at least one associative polymer comprising at least one $C_8$-$C_{30}$ fatty chain may be chosen from anionic, cationic, amphoteric and non-ionic associative polymers. For example, the at least one associative polymer comprising at least one $C_8$-$C_{30}$ fatty chain is chosen from anionic, cationic and non-ionic associative polymers.

The anionic associative polymers may, for example, be chosen from:
(I) polymers comprising at least one hydrophilic unit and at least one allyl ether unit comprising at least one fatty chain, for example, polymers whose at least one hydrophilic unit comprises at least one ethylenic unsaturated anionic monomeric unit, for example, chosen from vinylcarboxylic acid and, further, for example, chosen from an acrylic acid and a methacrylic acid, wherein the at least one allyl ether unit comprising at least one fatty chain is chosen from units of formula (V) below:

$$CH_2=CR'CH_2OB_nR \qquad (V)$$

wherein:

R' is chosen from H and $CH_3$;

B is an ethyleneoxy radical;

n is equal to zero or is an integer ranging from 1 to 100;

R is a hydrocarbon-based radical chosen from alkyl, arylalkyl, aryl, alkylaryl and cycloalkyl radicals, comprising from 8 to 30 carbon atoms, for example, 10 to 24 carbon atoms and, further, for example, from 12 to 18 carbon atoms.

For example, the unit of formula (V) may be chosen such that R' is H, n is equal to 10 and R is a stearyl ($C_{18}$) radical.

The anionic associative polymers of this type are described and prepared, according to an emulsion polymerization process, in Patent No. EP-0 216 479.

The anionic associative polymers may be chosen from polymers formed from 20% to 60% by weight of at least one monomer chosen from acrylic acid and methacrylic acid, from 5% to 60% by weight of lower alkyl (meth)acrylates, from 2% to 50% by weight of allyl ether comprising at least one fatty chain of formula (V), and from 0% to 1% by weight of a crosslinking agent which is a well-known copolymerizable unsaturated polyethylenic monomer, such as diallyl phthalate, allyl (meth)acrylate, divinylbenzene, (poly)ethylene glycol dimethacrylate and methylenebisacrylamide.

In one embodiment, the anionic associative polymers may be chosen from crosslinked terpolymers of methacrylic acid, of ethyl acrylate and of polyethylene glycol (10 EO) stearyl ether (Steareth-10), for example, those polymers sold by the company Allied Colloids under the names SALCARE SC 80 and SALCARE SC 90, which are aqueous 30% emulsions of a crosslinked terpolymer of methacrylic acid, of ethyl acrylate and of steareth-10 allyl ether (40/50/10).

(II) The anionic associative polymers may also be chosen from polymers comprising at least one hydrophilic unit of unsaturated olefinic carboxylic acid and at least one hydrophobic unit of a ($C_{10}$-$C_{30}$)alkyl ester of unsaturated carboxylic acid.

For example, these polymers are chosen from those in which the at least one hydrophilic unit of unsaturated olefinic carboxylic acid is chosen from units of formula (VI) below:

(VI)

wherein $R_1$ is chosen from H, $CH_3$, and $C_2H_5$, that is to say acrylic acid, methacrylic acid and ethacrylic acid units, and wherein the at least one hydrophobic unit of a ($C_{10}$-$C_{30}$) alkyl ester of unsaturated carboxylic acid is chosen from units of formula (VII) below:

(VII)

wherein:

$R_2$ is chosen from H, $CH_3$, and $C_2H_5$ (that is to say acrylate, methacrylate and ethacrylate units) and, for example, H (acrylate units) and $CH_3$ (methacrylate units) and $R_3$ is chosen from $C_{10}$-$C_{30}$ and, for example, $C_{12}$-$C_{22}$ alkyl radicals.

Examples of ($C_{10}$-$C_{30}$) alkyl esters of unsaturated carboxylic acids include lauryl acrylate, stearyl acrylate, decyl acrylate, isodecyl acrylate and dodecyl acrylate, and the corresponding methacrylates, lauryl methacrylate, stearyl methacrylate, decyl methacrylate, isodecyl methacrylate and dodecyl methacrylate.

Anionic associative polymers of this type are described and prepared, for example, according to U.S. Pat. Nos. 3,915,921 and 4,509,949.

The anionic associative polymers of this type may, for example, be chosen from polymers formed from a monomer mixture comprising:

(i) acrylic acid, (ii) at least one ester of formula (VII) described above wherein $R_2$ is chosen from H and $CH_3$, and $R_3$ is chosen from alkyl radicals comprising from 12 to 22 carbon atoms, and (iii) at least one crosslinking agent chosen from well-known copolymerizable polyethylenic unsaturated monomers, for example, diallyl phthalate, allyl(meth)acrylate, divinylbenzene, (poly)ethylene glycol dimethacrylate and methylenebisacrylamide.

The anionic associative polymers may be chosen from polymers comprising from 60% to 95% by weight of acrylic acid (hydrophilic unit), from 4% to 40% by weight of $C_{10}$-$C_{30}$ alkyl acrylate (hydrophobic unit) and from 0% to 6% by weight of crosslinking polymerizable monomeric units, and polymers comprising from 96% to 98% by weight of acrylic acid (hydrophilic unit), from 1% to 4% by weight of $C_{10}$-$C_{30}$ alkyl acrylate (hydrophobic unit) and from 0.1% to 0.6% by weight of crosslinking polymerizable monomeric units such as those described above.

Examples of such polymers include the products sold by the company Goodrich under the trade names PEMULEN TR1, PEMULEN TR2 and CARBOPOL 1382, and, further, for example, PEMULEN TR1, and the product sold by the company SEPPIC under the name COATEX SX.

(III) the anionic associative polymers may also be chosen from maleic anhydride/$C_{30}$-$C_{38}$ α-olefin/alkyl maleate terpolymers, such as the product (maleic anhydride/$C_{30}$-$C_{38}$ α-olefin/isopropyl maleate copolymer) sold under the name PERFORMA V 1608 by the company Newphase Technologies.

(IV) acrylic terpolymers comprising:

(a) from 20% to 70% by weight of a carboxylic acid comprising α,β-monoethylenic unsaturation, (b) from 20% to 80% by weight of a non-surfactant monomer comprising α,β-monoethylenic unsaturation other than (a), (c) from 0.5% to 60% by weight of a nonionic monourethane which is the product of reaction of a monohydric surfactant with a monoisocyanate comprising monoethylenic unsaturation, such as those polymers described in Patent Application No. EP-A-0 173 109 and, for example, the terpolymer described in Example 3, namely a methacrylic acid/methyl acrylate/behenyl dimethyl-meta-isopropenylbenzylisocyanate ethoxylated (40 EO) terpolymer, as an aqueous 25% dispersion.

(V) the anionic associative polymers may also be chosen from copolymers comprising as monomeric units, a carboxylic acid comprising α,β-monoethylenic unsaturation and an ester of a carboxylic acid comprising α,β-monoethylenic unsaturation and an oxyalkylenated fatty alcohol.

For example, these polymers also comprise as a monomer unit, an ester of a carboxylic acid comprising α,β-monoethylenic unsaturation and a $C_1$-$C_4$ alcohol.

An example of polymer of this type is ACULYN 22 sold by the company Rohm & Haas, which is a methacrylic acid/ethyl acrylate/stearyl methacrylate oxyalkylenated terpolymer.

(VI) the anionic associative polymers may also be chosen from anionic associative polyurethanes, such as VISCO-PHOBE DB 1000 from the company Union Carbide.

Examples of cationic associative polymers include:

(I) the cationic associative polyurethanes whose family has been described in French Patent Application No. 0 009 609. For example, these polymers may be chosen from those represented by the general formula (VIII) below:

$$R-X-(P)_n-[L-(Y)_m]_r-L'-(P')_p-X'-R' \quad (VIII)$$

wherein:
R and R', which may be identical or different, are each chosen from hydrophobic groups and a hydrogen atom;
X and X', which may be identical or different, are each chosen from groups comprising at least one amine functional group optionally bearing a hydrophobic group, or alternatively a group L";
L, L' and L", which may be identical or different, are each chosen from groups derived from a diisocyanate;
P and P', which may be identical or different, are each chosen from groups comprising at least one amine functional group optionally bearing a hydrophobic group;
Y is chosen from hydrophilic groups;
r is an integer ranging from 1 to 100, for example, from 1 to 50 and, further, for example, from 1 to 25;
n, m and p, which may be identical or different, are each integers ranging from 0 to 1000, wherein the molecule comprising at least one group chosen from protonated and quaternized amine functional groups and hydrophobic groups.

For example, in one embodiment, the only hydrophobic groups are the groups R and R' at the chain ends.

For example, the cationic associative polyurethanes may be chosen from those corresponding to formula (VIII) described above and wherein:
R and R', which may be identical or different, are each chosen from hydrophobic groups;
X and X', which may be identical or different, are each chosen from groups L";
n and p are integers ranging from 1 to 1000; and
L, L', L", P, P', Y and m have the meaning given above.

Further, for example, the cationic associative polyurethanes may be chosen from those corresponding to formula (VIII) above wherein:
R and R', which may be identical or different, are each chosen from hydrophobic groups;
X and X', which may be identical or different, are each chosen from groups L";
n and p are both equal to 0; and
L, L', L", Y and m have the meaning given above.

The fact that n and p are both equal to 0 means that these polymers do not comprise units derived from a monomer comprising an amine functional group, incorporated into the polymer during the polycondensation. The protonated amine functional groups of these polyurethanes result from the hydrolysis of excess isocyanate functional groups, at the chain end, followed by alkylation of the primary amine functional groups formed with alkylating agents comprising a hydrophobic group, i.e. compounds of the type RQ or R'Q, wherein R and R' are as defined above and Q is chosen from leaving groups such as a halide, a sulphate, etc.

Further, for example, the cationic associative polyurethanes may be chosen from those corresponding to formula (VIII) above wherein:
R and R', which may be identical or different, are each chosen from hydrophobic groups;
X and X', which may be identical or different, are each chosen from groups comprising a quaternary amine;
n and p are both equal to 0, and
L, L', Y and m have the meaning given above.

The number-average molecular mass of the cationic associative polyurethanes ranges, for example, from 400 to 500 000, further, for example, from 1000 to 400 000 and, even further, for example, from 1000 to 300 000.

With respect to the cationic associative polyurethanes, the expression "hydrophobic group" means a radical or polymer comprising a saturated or unsaturated, linear or branched hydrocarbon-based chain, which may comprise at least one entity chosen, for example, from P, O, N and S, and radicals comprising perfluoro or silicone chains. When the hydrophobic group is chosen from hydrocarbon-based radicals, it comprises at least 10 carbon atoms, for example, from 10 to 30 carbon atoms, further, for example, from 12 to 30 carbon atoms and, even further, for example, from 18 to 30 carbon atoms.

For example, the hydrocarbon-based group may be derived from a monofunctional compound.

For example, the hydrophobic group may be chosen from a fatty alcohols such as stearyl alcohol, dodecyl alcohol and decyl alcohol. It may also be chosen from hydrocarbon-based polymers such as, polybutadiene.

When X and/or X' is chosen from groups comprising a tertiary or quaternary amine, X and/or X' may be chosen from one of the following formulae:

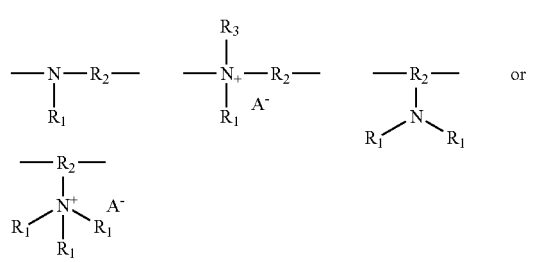

for X

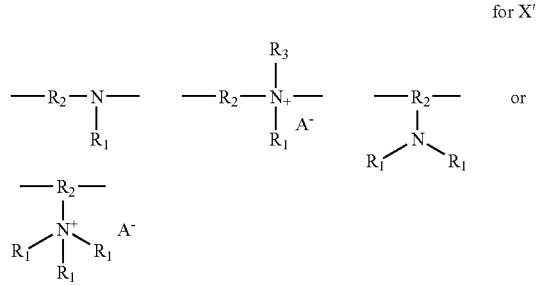

for X' wherein:
$R_2$, which may be identical or different, is chosen from linear and branched alkylene radicals comprising from 1 to 20 carbon atoms, optionally comprising a ring chosen from saturated and unsaturated rings, and an arylene radical, at least one of the carbon atoms of the alkylene radicals possibly being replaced with at least one hetero atom chosen from N, S, O and P;

$R_1$ and $R_3$, which may be identical or different, are each chosen from linear and branched $C_1$-$C_{30}$ alkyl and alkenyl radicals and an aryl radical, at least one of the carbon atoms possibly being replaced with at least one hetero atom chosen from N, S, O and P; and $A^-$ is a physiologically acceptable counter-ion.

The groups L, L' and L", which may be identical or different, are each chosen from groups of formula:

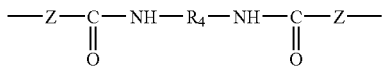

wherein:

Z is chosen from —O—, —S— and —NH—; and $R_4$ is chosen from linear and branched alkylene radicals comprising from 1 to 20 carbon atoms, optionally comprising a ring chosen from saturated and unsaturated rings and an arylene radical, at least one of the carbon atoms of the alkylene radicals possibly being replaced with at least one hetero atom chosen from N, S, O and P.

The groups P and P', which may be identical or different, comprising an amine functional group may be chosen from at least one of the following formulae:

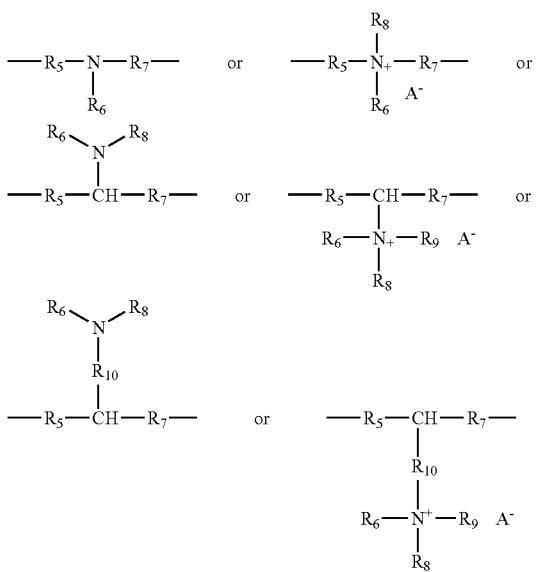

wherein:

$R_5$ and $R_7$ have the same meanings as $R_2$ defined above;

$R_6$, $R_8$ and $R_9$ have the same meanings as $R_1$ and $R_3$ defined above;

$R_{10}$, which may be identical or different, is chosen from linear and branched, optionally unsaturated alkylene groups which may comprise at least one hetero atom chosen from N, O, S and P, and $A^-$ is a physiologically acceptable counter-ion.

With regard to the meaning of Y, the term "hydrophilic group" means a polymeric or non-polymeric water-soluble group.

For example, when Y is not a polymer, mention may be made of ethylene glycol, diethylene glycol and propylene glycol.

When Y is a hydrophilic polymer it may be chosen, for example, from at least one of polyethers, sulphonated polyesters, and sulphonated polyamides. The hydrophilic polymer may, for example, be a polyether and, for example, a poly(ethylene oxide) or poly(propylene oxide).

The cationic associative polyurethanes of formula (VIII) are formed from diisocyanates and from various compounds with functional groups comprising labile hydrogen. The functional groups comprising labile hydrogen may be chosen from alcohol, primary and secondary amine and thiol functional groups forming, after reaction with the diisocyanate functional groups, polyurethanes, polyureas and polythioureas, respectively. As used herein, the term "polyurethanes" comprises these three types of polymer, for example, polyurethanes per se, polyureas and polythioureas, and also copolymers thereof.

A first type of compound involved in the preparation of the polyurethane of formula (VIII) is a compound comprising at least one unit comprising an amine functional group. This compound may be multifunctional, for example, the compound may be difunctional, that is to say that, according to one embodiment, this compound comprises two labile hydrogen atoms borne, for example, by a hydroxyl, primary amine, secondary amine or thiol functional groups. A mixture of multifunctional and difunctional compounds in which the percentage of multifunctional compounds is low may also be used.

As mentioned above, this compound may comprise more than one unit comprising an amine functional group. In this case, it is a polymer bearing a repetition of the unit comprising an amine functional group.

Compounds of this type may be chosen from those of the following formulae:

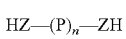

and

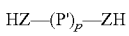

wherein Z, P, P', n and p are as defined above.

Examples of compounds comprising an amine functional group include N-methyldiethanolamine, N-tert-butyldiethanolamine and N-sulphoethyldiethanolamine.

The second compound involved in the preparation of the polyurethane of formula (VIII) is a diisocyanate corresponding to the formula below:

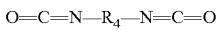

wherein $R_4$ is as defined above.

Examples of this compound include methylenediphenyl diisocyanate, methylenecyclohexane diisocyanate, isophorone diisocyanate, toluene diisocyanate, naphthalene diisocyanate, butane diisocyanate and hexane diisocyanate.

A third compound involved in the preparation of the polyurethane of formula (VIII) is a hydrophobic compound intended to form the terminal hydrophobic groups of the polymer of formula (VIII).

This compound comprises a hydrophobic group and a functional group comprising a labile hydrogen, for example a hydroxyl, primary or secondary amine, or thiol functional groups.

For example, this compound may be a fatty alcohol chosen from stearyl alcohol, dodecyl alcohol and decyl alcohol. When this compound comprises a polymeric chain, it may be, for example, α-hydroxylated hydrogenated polybutadiene.

The hydrophobic group of the polyurethane of formula (VIII) may also result from the quaternization reaction of the tertiary amine of the compound comprising at least one tertiary amine unit. Thus, the hydrophobic group is introduced via a quaternizing agent. This quaternizing agent is a compound chosen from RQ and R'Q, wherein R and R' are as defined above and Q is chosen from leaving groups such as a halide, a sulphate, etc.

The cationic associative polyurethane may also comprise a hydrophilic block. This block is provided by a fourth type of compound involved in the preparation of the polymer. This compound may be multifunctional, for example, products QUATRISOFT LM 200, QUATRISOFT LM-X 529-18-A, QUATRISOFT LM-X 529-18B® ($C_{12}$ alkyl) and QUATRISOFT LM-X 529-8®($C_{18}$ alkyl) sold by the company Amerchol and the products CRODACEL QM, CRODACEL QL ($C_{12}$ alkyl) and CRODACEL QS ($C_{18}$ alkyl) sold by the company Croda.

(III) cationic polyvinyllactams, the family of which was described in French Patent Application No. FR 0 101 106. These polymers comprise:
(a) at least one monomer chosen from vinyllactam and alkylvinyllactam monomers; and
(b) at least one monomer chosen from monomers of formulae (IX) and (X) below:

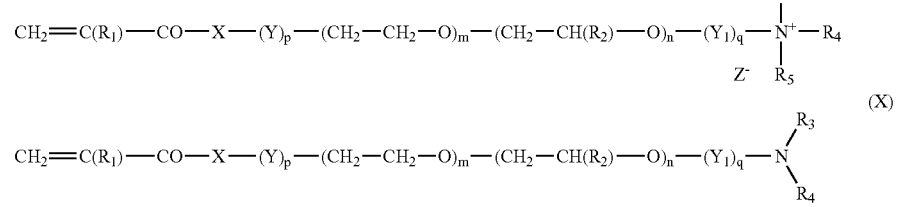

difunctional. It is also possible to have a mixture in which the percentage of the multifunctional compound is low.

The functional groups comprising a labile hydrogen are chosen from alcohol, primary and secondary amine and thiol functional groups. This compound may be a polymer terminated at the chain ends with one of these functional groups comprising a labile hydrogen.

By way of example, when the hydrophilic compound is not a polymer, mention may be made of ethylene glycol, diethylene glycol and propylene glycol.

When the hydrophilic compound is a hydrophilic polymer, it may be chosen from at least one of, for example, polyethers, sulphonated polyesters and sulphonated polyamides. The hydrophilic compound may, for example, be a polyether, such as poly(ethylene oxide) or poly(propylene oxide).

The hydrophilic group termed Y in formula (VIII) is optional. For example, the units comprising a quaternary amine or protonated functional group may suffice to provide the solubility or water-dispersibility required for this type of polymer in an aqueous solution.

Although the presence of a hydrophilic group Y is optional, cationic associative polyurethanes comprising such a group may, for example, be used.

(II) quaternized cellulose derivatives and polyacrylates comprising non-cyclic amino side groups.

The quaternized cellulose derivatives may, for example, be chosen from:
quaternized celluloses modified with groups comprising at least one fatty chain, such as alkyl, arylalkyl and alkylaryl groups comprising at least 8 carbon atoms and
quaternized hydroxyethylcelluloses modified with groups comprising at least one fatty chain, such as alkyl, arylalkyl and alkylaryl groups comprising at least 8 carbon atoms.

The alkyl radicals borne by the above quaternized celluloses or hydroxyethylcelluloses may, for example, comprise from 8 to 30 carbon atoms. The aryl radicals may, for example, be chosen from phenyl, benzyl, naphthyl and anthryl groups.

Examples of quaternized alkylhydroxyethylcelluloses comprising at least one $C_8$-$C_{30}$ fatty chain include the wherein:
X is chosen from an oxygen atom and a radical $NR_6$;
$R_1$ and $R_6$, which may be identical or different, are each chosen from a hydrogen atom and linear and branched $C_1$-$C_5$ alkyl radicals;
$R_2$, which may be identical or different, is chosen from linear and branched $C_1$-$C_4$ alkyl radicals;
$R_3$, $R_4$ and $R_5$, which may be identical or different, are each chosen from a hydrogen atom, linear and branched $C_1$-$C_{30}$ alkyl radicals, and radicals of formula (XI):

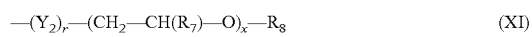

wherein:
Y, $Y_1$ and $Y_2$, which may be identical or different, are each chosen from linear and branched $C_2$-$C_{16}$ alkylene radicals;
$R_7$ is chosen from a hydrogen atom and linear and branched $C_1$-$C_4$ alkyl radicals and linear and branched $C_1$-$C_4$ hydroxyalkyl radicals;
$R_8$ is chosen from a hydrogen atom and linear and branched $C_1$-$C_{30}$ alkyl radicals;
p, q and r, which may be identical or different, are equal to either the value 0 or the value 1;
m and n, which may be identical or different, are each an integer ranging from 0 to 100;
x is an integer ranging from 1 to 100; and
Z is chosen from organic and mineral acid anions, with the proviso that:
at least one of the substituents $R_3$, $R_4$, $R_5$ or $R_8$ is chosen from linear and branched $C_9$-$C_{30}$ alkyl radicals;
if m or n is not equal to zero, then q is equal to 1;
if m or n are equal to zero, then p or q is equal to 0.

The cationic poly(vinyllactam) polymers disclosed herein may be crosslinked or non-crosslinked and may also be block polymers.

For example, the counterion $Z^-$ of the monomers of formula (IX) may be chosen from halide ions, phosphate ions, a methosulphate ion, and a tosylate ion.

For example, $R_3$, $R_4$ and $R_5$, which may be identical or different, are each chosen from a hydrogen atom and linear and branched $C_1$-$C_{30}$ alkyl radicals.

For example, the monomer b) is a monomer of formula (IX) and for example, m and n are equal to zero.

The vinyllactam or alkylvinyllactam monomer may, for example, be chosen from compounds of formula (XII):

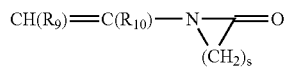  (XII)

wherein:
s is an integer ranging from 3 to 6;
$R_9$ is chosen from a hydrogen atom and $C_1$-$C_5$ alkyl radicals;
$R_{10}$ is chosen from a hydrogen atom and $C_1$-$C_5$ alkyl radicals; with the proviso that at least one of the radicals $R_9$ and $R_{10}$ is a hydrogen atom.

For example, the monomer (XII) may be vinylpyrrolidone.

The cationic poly(vinyllactam) polymers disclosed herein may also comprise at least one additional monomer, for example, chosen from cationic and nonionic monomers.

Examples of compounds that may be used in the compositions disclosed herein, include the following terpolymers comprising at least:

(a) one monomer unit of formula (XII);
(b) one monomer unit of formula (IX) wherein p=1, q=0, $R_3$ and $R_4$, which may be identical or different, are each chosen from a hydrogen atom and $C_1$-$C_5$ alkyl radicals and $R_5$ is chosen from $C_9$-$C_{24}$ alkyl radicals; and
c) a monomer of formula (X) wherein $R_3$ and $R_4$, which may be identical or different, are each chosen from a hydrogen atom and $C_1$-$C_5$ alkyl radicals.

For example, terpolymers comprising, by weight, 40% to 95% of monomer (a), 0.1% to 55% of monomer (c) and 0.25% to 50% of monomer (b) may be be used.

Such polymers are described in Patent Application No. WO 00/68282, the content of which relates to these polymers are incorporated herein by reference.

The cationic poly(vinyllactam) polymers may be chosen, for example, from vinyl pyrrolidone/dimethylaminopropylmethacrylamide/dodecyldimethylmethacrylamidopropylammonium tosylate terpolymers, vinylpyrrolidone/dimethylaminopropylmethacrylamide/cocoyldimethylmethacrylamidopropylammonium tosylate terpolymers, and vinylpyrrolidone/dimethylaminopropylmethacrylamide/lauryldimethylmethacrylamidopropylammonium tosylate and chloride terpolymers.

The weight-average molecular mass of the cationic poly(vinyllactam) polymers disclosed herein ranges, for example, from 500 to 20 000 000 g/mol, for example, from 200 000 to 2 000 000 g/mol and, even further, for example, from 400 000 to 800 000 g/mol.

The amphoteric associative polymers may, for example, be chosen from polymers comprising at least one non-cyclic cationic unit. For example, polymers prepared from or comprising 1 to 20 mol % of monomers comprising at least one fatty chain, for example, 1.5 to 15 mol % and even further, for example, from 1.5 to 6 mol %, relative to the total number of moles of monomers.

The amphoteric associative polymers may, for example, be chosen from those polymers that comprise, or are prepared by copolymerizing:

1) at least one monomer chosen from formulae (XIII) and (XIV):

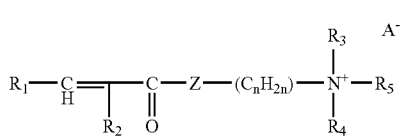  (XIII)

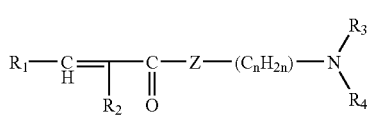  (XIV)

wherein:
$R_1$ and $R_2$, which may be identical or different, are each chosen from a hydrogen atom and a methyl radical;
$R_3$, $R_4$ and $R_5$, which may be identical or different, are each chosen from linear and branched alkyl radicals comprising from 1 to 30 carbon atoms;
Z is chosen from an NH group and an oxygen atom;
n is an integer ranging from 2 to 5; and
$A^-$ is an anion chosen from organic and mineral acids, such as a methosulphate anion and halides such as chloride and bromide;

2) at least one monomer of formula (XV)

$$R_6\text{—CH}=CR_7\text{—COOH} \quad (XV)$$

wherein:
$R_6$ and $R_7$, which may be identical or different, are each chosen from a hydrogen atom and a methyl radical; and 3) at least one monomer of formula (XVI):

$$R_6\text{—CH}=CR_7\text{—COXR}_8 \quad (XVI)$$

wherein:
$R_6$ and $R_7$, which may be identical or different, are each chosen from a hydrogen atom and a methyl radical;
X is chosen from an oxygen and a nitrogen atom; and
$R_8$ is chosen from linear and branched alkyl radicals comprising from 1 to 30 carbon atoms;

wherein at least one of the monomers of formula (XIII), (XIV) or (XV) comprise at least one fatty chain.

The monomers of formulae (XIII) and (XIV) may, for example, be chosen from:
dimethylaminoethyl methacrylate, dimethylaminoethyl acrylate;
diethylaminoethyl methacrylate, diethylaminoethyl acrylate;
dimethylaminopropyl methacrylate, dimethylaminopropyl acrylate; and
dimethylaminopropylmethacrylamide, dimethylaminopropylacrylamide, these monomers optionally being quaternized, for example with at least one radical chosen from $C_1$-$C_4$ alkyl halides and $C_1$-$C_4$ dialkyl sulphates.

For example, the monomer of formula (XIII) may be chosen from acrylamidopropyltrimethylammonium chloride and methacrylamidopropyltrimethylammonium chloride.

The monomers of formula (XIV) may be chosen from acrylic acid, methacrylic acid, crotonic acid and 2-methylcrotonic acid. For example, the monomer of formula (XIV) may be acrylic acid.

The monomers of formula (XIV) may, for example, be chosen from $C_{12}$-$C_{22}$ and, for example, $C_{16}$-$C_{18}$ alkyl acrylates and methacrylates.

The monomers constituting the fatty-chain amphoteric polymers disclosed herein may be already neutralized and/or quaternized.

The ratio of the number of cationic charges/anionic charges may, for example, be equal to about 1.

The amphoteric associative polymers disclosed herein may comprise from 1 mol % to 10 mol % and, for example, from 1.5 mol % to 6 mol % of the monomer comprising at least one fatty chain (monomer of formula (XIII), (XIV) or (XV)).

The weight-average molecular weight of the amphoteric associative polymers disclosed herein may range from 500 to 50 000 000 g/mol and, for example, from 10 000 to 5 000 000 g/mol.

The amphoteric associative polymers disclosed hereinn may also comprise other monomers such as nonionic monomers, for example, $C_1$-$C_4$ alkyl acrylates and methacrylates.

Amphoteric associative polymers disclosed herein are described and prepared, for example, in Patent Application No. WO 98/44012.

The amphoteric associative polymers disclosed herein may, for example, be chosen from acrylic acid/(meth)acrylamidopropyltrimethylammonium chloride/stearyl methacrylate terpolymers.

The nonionic associative polymers may, for example, be chosen from:
(1) celluloses modified with groups comprising at least one fatty chain; examples of these polymers include:
hydroxyethylcelluloses modified with groups comprising at least one fatty chain, such as alkyl, arylalkyl and alkylaryl groups, wherein the alkyl groups may, for example, be chosen from $C_8$-$C_{22}$ alkyl groups, such as the product NATROSOL PLUS GRADE 330 CS ($C_{16}$ alkyls) sold by the company Aqualon, and the product BERMOCOLL EHM 100 sold by the company Berol Nobel,
polymers modified with alkylphenyl polyalkylene glycol ether groups, such as the product AMERCELL POLYMER HM-1500 (nonylphenyl polyethylene glycol (15) ether) sold by the company Amerchol;
(2) hydroxypropyl guars modified with groups comprising at least one fatty chain, such as the product ESAFLOR HM 22 ($C_{22}$ alkyl chain) sold by the company Lamberti, and the products RE210-18 ($C_{14}$ alkyl chain) and RE205-1 ($C_{20}$ alkyl chain) sold by the company Rhône-Poulenc;
(3) copolymers of vinylpyrrolidone and of fatty-chain hydrophobic monomers; examples of these copolymers include:
the products ANTARON V216 and GANEX V216 (vinylpyrrolidone/hexadecene copolymer) sold by the company I.S.P.,
the products ANTARON V220 and GANEX V220 (vinylpyrrolidone/eicosene copolymer) sold by the company I.S.P.;
(4) copolymers of $C_1$-$C_6$ alkyl methacrylates and acrylates and amphiphilic monomers comprising at least one fatty chain, such as, the oxyethylenated methyl acrylate/stearyl acrylate copolymer sold by the company Goldschmidt under the name ANTIL 208;
(5) copolymers of hydrophilic methacrylates and acrylates and hydrophobic monomers comprising at least one fatty chain, such as, the polyethylene glycol methacrylate/lauryl methacrylate copolymer;
(6) polyurethane polyethers comprising in their chain both hydrophilic blocks, for example, polyoxyethylenated hydrophilic blocks and hydrophobic blocks comprising at least one sequence chosen from aliphatic sequences, cycloaliphatic sequences, and aromatic sequences; and
(7) polymers with an aminoplast ether skeleton comprising at least one fatty chain, such as the PURE THIX compounds sold by the company Sud-Chemie.

For example, the polyurethane polyethers may comprise at least two hydrocarbon-based lipophilic chains comprising from 6 to 30 carbon atoms, separated by a hydrophilic block, the hydrocarbon-based chains possibly being pendent chains, or chains at the end of the hydrophilic block. For example, it is possible for the polyurethane polyethers to comprise at least one pendent chain. Further, the polyurethane polyethers may comprise a hydrocarbon-based chain at one end or at both ends of a hydrophilic block.

The polyurethane polyethers may be in multiblock form, for example, in triblock form. The hydrophobic blocks may be at each end of the chain (for example: triblock copolymer with a hydrophilic central block) or distributed both at the ends and in the chain (for example: multiblock copolymer). These same polymers may also be chosen from graft polymers and starburst polymers.

The nonionic fatty-chain polyurethane polyethers may be triblock copolymers wherein the hydrophilic block is a polyoxyethylenated chain comprising from 50 to 1000 oxyethylene groups. The nonionic polyurethane polyethers may comprise a urethane linkage between the hydrophilic blocks, whence arises the name.

For example, the nonionic fatty-chain polyurethane polyethers may also be chosen from those polymers wherein the hydrophilic blocks are linked to the lipophilic blocks via other chemical bonds.

Examples of nonionic fatty-chain polyurethane polyethers that may be used in the compositions disclosed herein, include RHEOLATE 205 comprising a urea functional group, sold by the company Rheox, and RHEOLATES 208, 204 and 212, and ACRYSOL RM 184.

Further examples include the product ELFACOS T210 comprising at least one $C_{12\text{-}14}$ alkyl chain, and the product ELFACOS T212 comprising at least one $C_{18}$ alkyl chain, from Akzo.

The product DW 1206B from Rohm & Haas comprising at least one $C_{20}$ alkyl chain and a urethane linkage, sold at a solids content of 20% in water, may also be used.

It is also possible to use solutions or dispersions of these polymers, for example, in water or in an aqueous-alcoholic medium. Examples of such polymers that may be used include RHEOLATE 255, RHEOLATE 278 and RHEOLATE 244 sold by the company Rheox. The products DW 1206F and DW 1206J sold by the company Rohm & Haas may also be used.

The polyurethane polyethers that may be used in the compositions disclosed herein may be chosen, for example, from those described in the article by G. Fonnum, J. Bakke and Fk. Hansen—Colloid Polym. Sci 271, 380-389 (1993).

For example, the polyurethane polyether may be chosen from those that may be obtained by polycondensation of at least three compounds comprising (i) at least one polyethylene glycol comprising from 150 to 180 mol of ethylene oxide, (ii) stearyl alcohol or decyl alcohol, and (iii) at least one diisocyanate.

Such polyurethane polyethers are sold, for example, by the company Rohm & Haas under the names ACULYN 46 and ACULYN 44 [ACULYN 46 is a polycondensate of (i) polyethylene glycol comprising 150 or 180 mol of ethylene oxide, (ii) stearyl alcohol and (iii) methylenebis(4-cyclohexyl isocyanate) (SMDI), in an amount of 15% by weight, in a matrix of 4% by weight of maltodextrin and 81% by weight of water, wherein the weight percentages are relative to the total weight of the matrix; Aculyn 44® is a polycondensate of (i) polyethylene glycol comprising 150 or 180 mol of ethylene oxide, (ii) decyl alcohol and (iii) methylenebis(4-cyclohexylisocyanate) (SMDI), in an amount of 35% by weight, in a mixture of 39% by weight of propylene glycol and 26% by weight of water, wherein the weight percentages are relative to the total weight of the mixture].

In one embodiment, the at least one associative polymer comprising at least one $C_8$-$C_{30}$ fatty chain is chosen from nonionic and cationic associative polymers and, for example, from polyether polyurethanes comprising hydrophilic and hydrophobic blocks, polymers comprising an aminoplast ether skeleton comprising at least one fatty chain, cationic associative polyurethanes, quaternized cellulose derivatives comprising at least one fatty chain, and cationic polyvinyllactams.

In another embodiment, the at least one associative polymer comprising at least one $C_8$-$C_{30}$ fatty chain is chosen from quaternized ($C_8$-$C_{30}$)alkylhydroxyethylcelluloses and, for example, laurylhydroxyethylcellulose.

The composition disclosed herein may comprise, in addition to the at least one coupler chosen from 2-chloro-6-methyl-3-aminophenol and addition salts thereof, at least one additional coupler chosen from couplers conventionally used for the oxidation dyeing of keratin fibres. For example, the at least one additional coupler may be chosen from meta-phenylenediamines, meta-aminophenols other than 2-chloro-6-methyl-3-aminophenol, meta-diphenols, naphthalene-based couplers, heterocyclic couplers, and addition salts thereof.

Examples of the at least one additional coupler include 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino) toluene, and acid addition salts thereof.

The at least one oxidation base may be present in the composition disclosed herein in an amount ranging from 0.001% to 10% by weight, and, for example, from 0.005% to 6% by weight, relative to the total weight of the composition.

The at least one associative polymer comprising at least one $C_8$-$C_{30}$ fatty chain may be present in an amount ranging from 0.01% to 10% by weight, relative to the total weight of the composition, for example, from 0.1% to 5% by weight, and even further, for example, from 0.5% to 3% by weight, relative to the total weight of the composition.

In the compositions disclosed herein, the at least one coupler chosen from 2-chloro-6-methyl-3-aminophenol and addition salts thereof may be present in an amount ranging from 0.001% to 10% by weight, for example, from 0.005% to 6% by weight, relative to the total weight of the composition.

For example, the addition salts of the at least one oxidation base and of the at least one coupler chosen from 2-chloro-6-methyl-3-aminophenol and the at least one additional coupler that may be used in the compositions disclosed herein are chosen from addition salts with an acid, such as the hydrochlorides, hydrobromides, sulphates, citrates, succinates, tartrates, lactates, tosylates, benzenesulphonates, phosphates and acetates, and addition salts with a base, such as sodium hydroxide, potassium hydroxide, aqueous ammonia, amines and alkanolamines.

The compositions disclosed herein may also comprise at least one direct dye that may be chosen, for example, from nitrobenzene dyes, azo direct dyes and methine direct dyes. These at least one direct dye may be chosen from nonionic, anionic and cationic direct dyes.

In one embodiment, the medium that is suitable for dyeing, also known as a dye support, comprises water and mixtures of water and at least one organic solvent to dissolve the compounds that would not be sufficiently soluble in the water. Examples of the at least one organic solvent include $C_1$-$C_4$ lower alkanols, such as ethanol and isopropanol; polyols and polyol ethers, such as, 2-butoxyethanol, propylene glycol, propylene glycol monomethyl ether, diethylene glycol monoethyl ether and monomethyl ether, and also aromatic alcohols, for example, benzyl alcohol and phenoxyethanol.

The at least one organic solvent may be present in an amount ranging from 1% to 40% by weight and, for example, from 5% to 30% by weight, relative to the total weight of the composition.

The compositions disclosed herein may also comprise at least one adjuvant conventionally used in hair dye compositions, for example, chosen from anionic, cationic, nonionic, amphoteric and zwitterionic surfactants; anionic, cationic, nonionic, amphoteric and zwitterionic polymers; mineral and organic thickeners, other than anionic, cationic, nonionic and amphoteric associative polymers; antioxidants; penetrating agents; sequestering agents; fragrances; buffers; dispersants; conditioners such as volatile and non-volatile, modified and unmodified silicones; film-forming agents; ceramides; preserving agents; and opacifiers.

The at least one adjuvant may be present in an amount ranging from 0.001% to 20% by weight, relative to the weight of the composition.

Needless to say, a person skilled in the art will take care to select this or these additional optional compound(s) such that the advantageous properties intrinsically associated with the compositions disclosed herein is not, or are not substantially, adversely affected by the envisaged addition(s).

In one embodiment, the pH of the compositions disclosed herein ranges from 3 to 12 and, for example, from 5 to 11. It may be adjusted to the desired value by means of at least one agent chosen from acidifying and basifying agents usually used for dyeing keratin fibres and standard buffer systems.

The acidifying agents may, for example, be chosen from mineral and organic acids, such as hydrochloric acid, orthophosphoric acid, sulphuric acid, carboxylic acids, such as acetic acid, tartaric acid, citric acid and lactic acid, and sulphonic acids.

The basifying agents may, for example, be chosen from aqueous ammonia, alkaline carbonates, alkanolamines such as monoethanolamine, diethanolamine and triethanolamine and derivatives thereof, sodium hydroxide, potassium hydroxide and the compounds of formula (XVI) below:

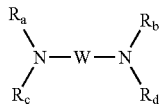 (XVI)

wherein W is chosen from propylene residues optionally substituted with at least one entity chosen from hydroxyl groups and $C_1$-$C_4$ alkyl radicals; $R_a$, $R_b$, $R_c$ and $R_d$, which may be identical or different, are each chosen from a hydrogen atom and $C_1$-$C_4$ alkyl radicals and $C_1$-$C_4$ hydroxyalkyl radicals.

The composition according to the invention may be provided in various forms, for example, chosen from liquids, creams and gels, and any other forms that is suitable for dyeing keratin fibres, such as human hair.

One embodiment relates to a process comprising applying at least one composition disclosed herein to the keratin fibres, wherein a color is developed using at least one oxidizing agent. The color may be revealed at acidic, neutral or alkaline pH and the at least one oxidizing agent may be added to the at least one composition disclosed herein at the time of use, or it may be introduced using at least one oxidizing composition comprising it, applied simultaneously with or sequentially to the at least one composition.

In one embodiment, the at least one composition disclosed herein is mixed, for example, at the time of use, with at least one oxidizing composition comprising, in a medium that is suitable for dyeing, at least one oxidizing agent, the at least one oxidizing agent is present in an amount that is sufficient to develop a coloration. The mixture obtained is applied to the keratin fibres. After a leave-in time of 3 to 50 minutes and, for example, from 5 to 30 minutes, the keratin fibres are rinsed, washed with shampoo, rinsed again and then dried.

The at least one oxidizing agent may be chosen from those conventionally used for the oxidation dyeing of keratin fibres, for example, hydrogen peroxide, urea peroxide, alkali metal bromates, persalts such as perborates and persulphates, peracids, and oxidase enzymes, such as, peroxidases, 2-electron oxidoreductases such as uricases, and 4-electron oxygenases, for example, laccases. In one embodiment, hydrogen peroxide may be used.

The at least one oxidizing composition may also comprise at least one adjuvant conventionally used in hair dye compositions and as defined above.

In one embodiment, the pH of the at least one oxidizing composition comprising the at least one oxidizing agent is such that, after mixing with the at least one composition, the pH of the resulting composition applied to the keratin fibres ranges from 3 to 12 and, for example, from 5 to 11. It may be adjusted to the desired value by means of at least one agent chosen from acidifying and basifying agents usually used in the dyeing of keratin fibres and as defined above.

The ready-to-use composition that is finally applied to the keratin fibres may be provided in various forms, such as in a form chosen from liquids, creams and gels, and any other forms that are suitable for dyeing keratin fibres, such as, human hair.

Also disclosed herein is a multi-compartment device or "kit" for dyeing comprising at least one first compartment comprising the at least one composition disclosed herein and at least one second compartment comprising at least one oxidizing composition. This device may be equipped with a means for applying the desired mixture to the hair, such as the devices described in Patent No. FR 2 586 913.

Using this device, it is possible to dye keratin fibres using a process that involves mixing the at least one composition disclosed herein with at least one oxidizing agent as defined above, and applying the mixture obtained to the keratin fibres for a time that is sufficient to develop the desired coloration.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained herein. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope are approximations, the numerical values set forth in the specific examples are reported as precisely as possible. Any numerical value, however, inherently contain certain errors necessarily resulting from the standard deviation found in their respective testing measurements.

The examples that follow serve to illustrate the various embodiments disclosed herein without, however, being limiting in nature.

EXAMPLES

The compositions below were prepared:

|  | Example | | | |
| --- | --- | --- | --- | --- |
|  | 1 | 2 | 3 | 4 |
| 2-Chloro-6-methyl-3-aminophenol | 1.26 g | 1.26 g | 1.26 g | 1.26 g |
| para-Aminophenol | 0.872 g | | | |
| 3-Methyl-4-aminophenol | | | | 0.984 g |
| para-Phenylenediamine | | | 0.864 g | |
| para-Tolylenediamine | | 0.976 g | | |
| Aculyn 44 ® or Aculyn 46 ® sold by Rohm & Haas | 4 g A.M. | | | |

| -continued | | | | |
|---|---|---|---|---|
| Pemulen TR1 ® sold by Goodrich | | 3.8 g A.M. | | |
| Quadrisoft LM 200 ® sold by Amerchol | | | 3.8 g A.M. | 3.8 g A.M. |
| Dye support | (*) | (*) | (*) | (*) |
| Demineralized water qs | 100 g | 100 g | 100 g | 100 g |

| (*): common dye support | |
|---|---|
| Mixture of $C_{18}$ to $C_{24}$ linear alcohols (7/58/30/6: $C_{18}/C_{20}/C_{22}/C_{24}$ - alcohol content >95%) | 3.0 g |
| Mixture of oxyethylenated (30 EO) $C_{18}$ to $C_{24}$ linear alcohols (7/58/30/6: $C_{18}/C_{20}/C_{22}/C_{24}$ - alcohol content >95%) | 1.0 g |
| Oxyethylenated (2 EO) stearyl alcohol | 4.5 g |
| Oxyethylenated (21 EO) stearyl alcohol | 1.75 g |
| Cationic polymer W | 4.0 g A.M. |
| Oleic acid | 2.6 g |
| Crosslinked polyacrylic acid (Carbopol 980 from Goodrich) | 0.6 g |
| Coconut acid monoisopropanolamide | 3.0 g |
| Hexylene glycol | 6.0 g |
| Sodium metabisulphite | 0.71 g |
| EDTA | 0.2 g |
| tert-Butylhydroquinone | 0.3 g |
| Monoethanolamine | 1.0 g |
| Aqueous ammonia containing 20% $NH_3$ | 11.0 g |
| Fragrance | qs |

The oxidizing composition below was prepared:

| Fatty alcohol | 2.3 g |
|---|---|
| Oxyethylenated fatty alcohol | 0.6 g |
| Fatty amide | 0.9 g |
| Glycerol | 0.5 g |
| Hydrogen peroxide | 7.5 g |
| Fragrance | qs |
| pH agent, pH = 3 | qs |
| Demineralized water, qs | 100 g |

The composition was mixed extemporaneously with one and a half times its weight of oxidizing composition.

The mixture thus prepared was applied to locks of natural grey hair containing 90% white hairs, at a rate of 30 g per 3 g of hair, for 30 minutes. The hair was rinsed, washed with a standard shampoo and dried.

The hair coloration was evaluated visually. The shades obtained are given in the table below.

| | Example | | | |
|---|---|---|---|---|
| | 1 | 2 | 3 | 4 |
| Tone height | Blond | Dark blond | Dark blond | Blond |
| Glint | Coppery red | Purplish | Dark purple | Red |

What is claimed is:

1. A composition comprising, in a suitable dyeing medium:
    at least one coupler chosen from 2-chloro-6-methyl-3-aminophenol and addition salts thereof;
    at least one oxidation base; and
    at least one associative polymer comprising at least one $C_8$-$C_{30}$ fatty chain.

2. The composition according to claim 1, wherein the at least one oxidation base is chosen from para-phenylenediamines, double bases, para-aminophenols, ortho-aminophenols and heterocyclic oxidation bases, and addition salts thereof.

3. The composition according to claim 2, wherein the para-phenylenediamines are chosen from compounds of formula (I), and addition salts thereof:

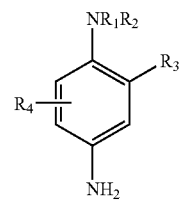

wherein:
    $R^1$ is chosen from a hydrogen atom, $C_1$-$C_4$ alkyl radicals, $C_1$-$C_4$ monohydroxyalkyl radicals, $C_2$-$C_4$ polyhydroxyalkyl radicals, $(C_1$-$C_4)$alkoxy$(C_1$-$C_4)$alkyl radicals, $C_1$-$C_4$ alkyl radicals substituted with at least one nitrogenous group, a phenyl radical, and a 4'-aminophenyl radical;
    $R_2$ is chosen from a hydrogen atom, $C_1$-$C_4$ alkyl radicals, $C_1$-$C_4$ monohydroxyalkyl radicals, $C_2$-$C_4$ polyhydroxyalkyl radicals, $(C_1$-$C_4)$alkoxy$(C_1$-$C_4)$alkyl radicals, and $C_1$-$C_4$ alkyl radicals substituted with at least one nitrogenous group;
    $R_1$ and $R_2$ may form together, with the nitrogen atom to which they are attached, a heterocycle chosen from 5- to 8-membered heterocycles optionally substituted with at least one group chosen from $C_1$-$C_4$ alkyl radicals, amino, hydroxyalkyl radicals, and $C_1$-$C_4$ trialkylammonium radicals;
    $R_3$ is chosen from a hydrogen atom, halogen atoms, $C_1$-$C_4$ alkyl radicals, $C_1$-$C_4$ monohydroxyalkyl radicals, $C_1$-$C_4$ hydroxyalkoxy radicals, acetylamino$(C_1$-$C_4)$alkoxy radicals, mesylamino$(C_1$-$C_4)$alkoxy radicals, and carbamoylamino$(C_1$-$C_4)$alkoxy radicals; and $R_4$ is chosen from a hydrogen atom, halogen atoms, and $C_1$-$C_4$ alkyl radicals.

4. The composition according to claim 3, wherein, in $R_3$, the halogen atoms are chosen from chlorine, bromine, iodine, and fluorine atoms.

5. The composition according to claim 3, wherein the para-phenylenediamines of formula (I) are chosen from para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-N,N-bis(β-hydroxyethyl)-2-chloroaniline, 2-β-hydroxyethyl)-para-phenylenediamine, 2-fluoro-para-phenylenediamine, 2-isopropyl-para-pherylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-(β-hydroxy-ethyloxy)-para-phenylenediamine, 2-(β-acetylaminoethyloxy)-para-phenylenediamine, N-(β-methoxyethyl)-para-phenylenediamine and addition salts thereof.

6. The composition according to claim 2, wherein the double bases are chosen from compounds corresponding to formula (II), and addition salts thereof:

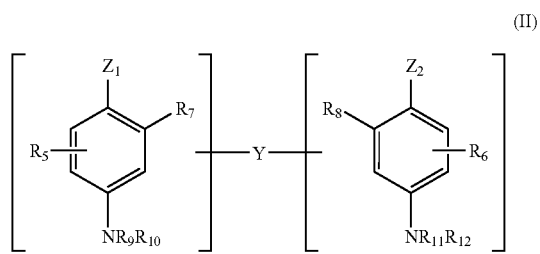

wherein:
  $Z_1$ and $Z_2$, which may be identical or different, are each chosen from hydroxyl and amino radicals optionally substituted with at least one entity chosen from $C_1$-$C_4$ alkyl radicals and linker arm Y;
  linker arm Y is chosen from linear and branched alkylene chains comprising from 1 to 14 carbon atoms, wherein the alkylene chains may be interrupted by or terminated with at least one entity chosen from nitrogenous groups and hetero atoms, and optionally substituted with at least one radical chosen from hydroxyl and $C_1$-$C_6$ alkoxy radicals;
  $R_5$ and $R_6$, which may be identical or different, are each chosen from a hydrogen atom, halogen atoms, $C_1$-$C_4$ alkyl radicals, $C_1$-$C_4$ monohydroxyalkyl radicals, $C_2$-$C_4$ polyhydroxyalkyl radicals, $C_1$-$C_4$ aminoalkyl radicals, and linker arm Y; and
  $R_7$, $R_8$, $R_9$, $R_{10}$, $R_{11}$ and $R_{12}$, which may be identical or different, are each chosen from a hydrogen atom, linker arm Y, $C_1$-$C_4$ alkyl radicals, and $C_1$-$C_4$ monohydroxyalkyl radicals;
it being understood that the compounds of formula (II) comprise only one linker arm Y per molecule.

7. The composition according to claim 6, wherein, in linker arm Y, the hetero atoms are chosen from oxygen, sulphur and nitrogen atoms.

8. The composition according to claim 6, wherein the double bases of formula (II) are chosen from N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)-tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,5-dioxaoctane, 4-amino-6-[(5'-amino-2'-hydroxy-3'-methylphenyl)methyl]-2-methylphenol, bis(5-amino-2-hydroxyphenyl)methane, and addition salts thereof.

9. The composition according to claim 2, wherein the para-aminophenols are chosen from compounds corresponding to formula (III) below, and addition salts thereof:

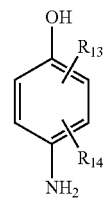

wherein:
  $R_{13}$ is chosen from a hydrogen atom, halogen atoms, $C_1$-$C_4$ alkyl radicals, $C_1$-$C_4$ monohydroxyalkyl radicals, ($C_1$-$C_4$)alkoxy($C_1$-$C_4$)alkyl radicals, $C_1$-$C_4$ aminoalkyl radicals, and hydroxy($C_1$-$C_4$)alkylamino($C_1$-$C_4$)alkyl radicals; and
  $R_{14}$ is chosen from a hydrogen atom, halogen atoms, $C_1$-$C_4$-alkyl radicals, $C_1$-$C_4$ monohydroxyalkyl radicals, $C_2$-$C_4$ polyhydroxyalkyl radicals, $C_1$-$C_4$ aminoalkyl radicals, $C_1$-$C_4$ cyanoalkyl radicals and ($C_1$-$C_4$)alkoxy-($C_1$-$C_4$)alkyl radicals;
it being understood that at least one of the radicals $R_{13}$ and $R_{14}$ is a hydrogen atom.

10. The composition according to claim 9, wherein the para-aminophenols are chosen from para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, 4-amino-2-chlorophenol, 4-amino-2,6-dichlorophenol, and addition salts thereof.

11. The composition according to claim 2, wherein the ortho-aminophenols are chosen from 2-aminophenol, 2-amino-5-methylphenol, 2-amino-6-methylphenol, 5-acetamido-2-aminophenol, and addition salts thereof.

12. The composition according to claim 2, wherein the heterocyclic bases are chosen from pyridine derivatives, pyrimidine derivatives, pyrazole derivatives, pyrazolo-pyrimidine derivatives, and addition salts thereof.

13. The composition according to claim 1, wherein the at least one associative polymer comprising at least one $C_8$-$C_{30}$ fatty chain comprises at least one hydrophilic region.

14. The composition according to claim 1, wherein the at least one associative polymer comprising at least one $C_8$-$C_{30}$ fatty chain is derived from free-radical polymerization;

polycondensation starting with at least one monomer, wherein at least one of the monomers comprises at least one $C_8$-$C_{30}$ fatty chain; or grafting onto a polymer a compound comprising at least one $C_8$-$C_{30}$ fatty chain.

15. The composition according to claim 1, wherein the at least one associative polymer comprising at least one $C_8$-$C_{30}$ fatty chain is chosen from thickening polymers.

16. The composition according to claim 1, wherein the at least one associative polymer comprising at least one $C_8$-$C_{30}$ fatty chain is chosen from anionic, cationic, amphoteric and non-ionic associative polymers.

17. The composition according to claim 16, wherein the at least one the associative polymer comprising at least one $C_8$-$C_{30}$ fatty chain is chosen from anionic associative polymers.

18. The composition according to claim 17, wherein the anionic associative polymers comprise at least one hydrophilic unit of an olefinic unsaturated carboxylic acid and at least one hydrophobic unit of a ($C_{10}$-$C_{30}$)alkyl ester of unsaturated carboxylic acid.

19. The composition according to claim 18, wherein the anionic associative polymers comprise monomeric units chosen from acrylic acid; acrylic and methacrylic acid ($C_{12}$-$C_{22}$)alkyl esters; and crosslinking polymerizable monomeric units.

20. The composition according to claim 19, wherein the anionic associative polymers comprise from 60% to 95% by weight of acrylic acid, from 4% to 40% by weight of $C_{10}$-$C_{30}$ alkyl acrylate and from 0 to 6% by weight of copolymerizable polyethylenic unsaturated monomeric units.

21. The composition according to claim 19, wherein the anionic associative polymers comprise from 96% to 98% by weight of acrylic acid, from 1% to 4% by weight of $C_{10}$-$C_{30}$ alkyl acrylate and from 0.1% to 0.6% by weight of crosslinking polymerizable monomeric units.

22. The composition according to claim 17, wherein the anionic associative polymers are chosen from polyurethanes.

23. The composition according to claim 16, wherein the at least one associative polymer comprising at least one $C_8$-$C_{30}$ fatty chain is chosen from cationic associative polymers.

24. The composition according to claim 23, wherein the cationic associative polymers are chosen from quaternized cellulose derivatives.

25. The composition according to claim 24, wherein the quaternized cellulose derivatives are chosen from quaternized hydroxyethylcelluloses modified with at least one group comprising at least one fatty chain.

26. The composition according to claim 25, wherein the at least one fatty chain is chosen from alkyl radicals comprising from 8 to 30 carbon atoms.

27. The composition according to claim 23, wherein the cationic associative polymers are chosen from polyurethanes.

28. The composition according to claim 17, wherein the at least one associative polymer comprising at least one $C_8$-$C_{30}$ fatty chain is a non-ionic associative polymer chosen from polyurethane polyethers.

29. The composition according to claim 28, wherein the polyurethane polyethers are chosen from polycondensates of (i) polyethylene glycol comprising 150 or 180 mol of ethylene oxide, (ii) stearyl alcohol and (iii) at least one diisocyanate.

30. The composition according to claim 29, wherein the polyurethane polyethers are chosen from polycondensates of (i) polyethylene glycol comprising 150 or 180 mol of ethylene oxide, (ii) stearyl alcohol and (iii) methylenebis(4-cyclohexyl isocyanate) (SMDI), in an amount of 15% by weight, in a matrix of 4% by weight of maltodextrin and 81% by weight of water, wherein the weight percentages are relative to the total weight of the matrix.

31. The composition according to claim 28, wherein the polyurethane polyethers are chosen from polycondensates of (i) polyethylene glycol comprising 150 or 180 mol of ethylene oxide, (ii) decyl alcohol, and (iii) at least one diisocyanate.

32. The composition according to claim 31, wherein the polyurethane polyethers are chosen from polycondensates of (i) polyethylene glycol comprising 150 or 180 mol of ethylene oxide, (ii) decyl alcohol, and (iii) methylenebis(4-cyclohexyl isocyanate) (SMDI), in an amount of 35% by weight, in a mixture of 39% by weight of propylene glycol and 26% by weight of water, wherein the weight percentages are relative to the total weight of the mixture.

33. The composition according to claim 1, further comprising at least one additional coupler chosen from meta-phenylenediamines, meta-aminophenols other than 2-chloro-6-methyl-3-aminophenol, meta-diphenols, naphthalene-based couplers, heterocyclic couplers, and addition salts thereof.

34. The composition according to claim 1, wherein the at least one oxidation base is present in an amount ranging from 0.001% to 10% by weight, relative to the total weight of the composition.

35. The composition according to claim 34, wherein the at least one oxidation base is present in an amount ranging from 0.005% to 6% by weight, relative to the total weight of the composition.

36. The composition according to claim 1, wherein the at least one associative polymer comprising at least one $C_8$-$C_{30}$ fatty chain is present in an amount ranging from 0.01% and 10% by weight, relative to the total weight of the composition.

37. The composition according to claim 36, wherein the at least one associative polymer comprising at least one $C_8$-$C_{30}$ fatty chain is present in an amount ranging from 0.1% and 5% by weight, relative to the total weight of the composition.

38. The composition according to claim 37, wherein the at least one associative polymer comprising at least one $C_8$-$C_{30}$ fatty chain is present in an amount ranging from 0.5% and 3% by weight, relative to the total weight of the composition.

39. The composition according to claim 1, wherein the at least one coupler chosen from 2-chloro-6-methyl-3-aminophenol and addition salts thereof is present in an amount ranging from 0.001% to 10% by weight, relative to the total weight of the composition.

40. The composition according to claim 39, wherein the at least one coupler chosen from 2-chloro-6-methyl-3-aminophenol and addition salts thereof is present in an amount ranging from 0.005% to 6% by weight, relative to the total weight of the composition.

41. The composition according to claim 1, further comprising at least one oxidizing agent.

42. The composition according to claim 41, wherein the at least one oxidizing agent is chosen from hydrogen peroxide, urea peroxide, alkali metal bromates, persalts, peracids and oxidase enzymes.

43. A process for the oxidation dyeing of keratin fibres comprising applying to the keratin fibers at least one composition comprising, in a suitable dyeing medium:

at least one coupler chosen from 2-chloro-6-methyl-3-aminophenol and addition salts thereof;

at least one oxidation base; and at least one associative polymer comprising at least one $C_8$-$C_{30}$ fatty chain, wherein a color is developed using at least one oxidizing agent.

44. The process according to claim 43, wherein the at least one oxidizing agent is chosen from hydrogen peroxide, urea peroxide, alkali metal bromates, persalts, peracids and oxidase enzymes.

45. The process according to claim 43, wherein the at least one oxidizing agent is mixed at the time of use with the at least one composition.

46. The process according to claim 43, wherein the at least one oxidizing agent is applied to keratin fibres in the form of at least one oxidizing composition, simultaneously with or sequentially to the at least one composition.

47. A multi-compartment device comprising, (i) at least one first compartment comprising at least one composition comprising, in a suitable dyeing medium:

at least one coupler chosen from 2-chloro-6-methyl-3-aminophenol and addition salts thereof;

at least one oxidation base; and at least one associative polymer comprising at least one $C_8$-$C_{30}$ fatty chain and (ii) at least one second compartment comprising at least one oxidizing agent.

48. A method for preparing a composition for the oxidation dyeing of keratin fibers comprising including in the composition, at least one coupler chosen from 2-chloro-6-methyl-3-aminophenol and addition salts thereof;

at least one oxidation base; and at least one associative polymer comprising at least one $C_8$-$C_{30}$ fatty chain.

49. A composition for the oxidation dyeing of keratin fibers comprising, in a suitable dyeing medium:

at least one coupler chosen from 2-chloro-6-methyl-3-aminophenol and addition salts thereof;

at least one oxidation base; and at least one associative polymer comprising at least one $C_8$-$C_{30}$ fatty chain, wherein the at least one coupler chosen from 2-chloro-6-methyl-3-aminophenol and addition salts thereof, the at least one oxidation base, and the at least one associative polymer comprising at least one $C_8$-$C_{30}$ fatty chain are each present in an amount effective for dyeing the keratin fibers.

* * * * *